United States Patent [19]

Sandefur et al.

[11] Patent Number: 4,515,947
[45] Date of Patent: May 7, 1985

[54] CYANOALKYLPIPERAZINES AND METHODS FOR THEIR PREPARATION AND USE

[75] Inventors: Louise O. Sandefur; Wojciech Slusarek, both of Rochester; Burton D. Wilson, Webster; Cataldo A. Maggiulli, Pittsford, all of N.Y.

[73] Assignee: Eastman Kodak Company, Rochester, N.Y.

[21] Appl. No.: 407,216

[22] Filed: Aug. 11, 1982

[51] Int. Cl.$^3$ .......................................... C07D 403/04
[52] U.S. Cl. ................................. 544/295; 544/230; 544/402
[58] Field of Search ............................. 544/295, 402

[56] References Cited

U.S. PATENT DOCUMENTS

| | | | |
|---|---|---|---|
| 2,415,787 | 2/1947 | Buck et al. | 544/402 |
| 2,543,972 | 3/1951 | Holtquist et al. | 544/295 |
| 3,196,155 | 7/1965 | Gailliot et al. | 424/250 |
| 3,398,151 | 8/1968 | Wu | 424/250 |
| 3,717,634 | 2/1973 | Wu et al. | 424/251 |
| 3,907,801 | 9/1975 | Wu et al. | 424/250 |
| 3,944,551 | 3/1976 | Regniet et al. | 544/295 |
| 3,976,776 | 8/1976 | Wu et al. | 424/251 |
| 4,256,888 | 3/1981 | Vanderbilt et al. | 544/334 |
| 4,259,334 | 3/1981 | Pascal et al. | 544/402 |

OTHER PUBLICATIONS

Hromatka, et al., "Chemical Abstracts", vol. 59, 1963, col. 1632c.
Caldwell, "Chemical Abstracts", vol. 64, 1966, col. 740e–740b.
Lespagnol, et al., "Chemical Abstracts", vol. 59, 1963, col. 8740c.
Howard et al., *J. Org. Chem.*, vol. 18, pp. 1484–1488 (1953).

*Primary Examiner*—Glennon H. Hollrah
*Assistant Examiner*—James H. Turnipseed
*Attorney, Agent, or Firm*—David F. Janci

[57] ABSTRACT

Novel cyanoalkylpiperazines are prepared by reacting piperazine with a haloalkylnitrile in the presence of an acid acceptor. The novel cyanoalkylpiperazines are advantageously employed to prepare 1-(cyanoalkyl)-4-(2-pyrimidyl)piperazines by reacting them with halopyrimidines in the presence of an acid acceptor.

22 Claims, No Drawings

CYANOALKYLPIPERAZINES AND METHODS FOR THEIR PREPARATION AND USE

BACKGROUND OF THE INVENTION

1. Field of the Invention

The invention relates to cyanoalkylpiperazines, methods for their preparation, and methods for their use in preparing 1-(cyanoalkyl)-4-(2-pyrimidyl)piperazines (which are in turn useful materials for producing compounds having pharmacological utility as tranquilizing and anti-emetic agents).

2. Description Relative to the Prior Art

It is known that 8-[ω-[4-(2-pyrimidyl)-1-piperazinyl]alkyl]-8-azaspiro[4.5]decane-7,9-diones represented by the structural formula

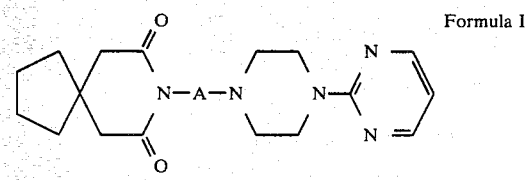

Formula I wherein A represents an alkylene group having from 2 to 6 carbon atoms, have pharmacological utility as tranquilizing and anti-emetic agents.

Methods are also known for preparing the compounds of Formula I by using, as starting materials, 1-(cyanoalkyl)-4-(2-pyrimidyl)piperazines represented by the structural formula

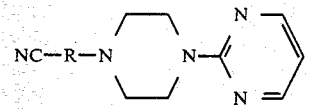

Formula II wherein R represents an alkylene group having from 1 to 5 carbon atoms. Such methods are described, for example, in U.S. Pat. Nos. 3,976,776; 3,907,801; 3,717,634; and 3,398,151, and the disclosures of these patents are hereby incorporated herein by reference.

The aforesaid patents, taken with Howard et al, *J. Org. Chem.*, Vol. 18, pp. 1484–1488 (1953) (which is referred to therein) also describe a method for preparing the compounds of Formula II. For example, for preparing 1-(3-cyanopropyl)-4-(2-pyrimidyl)piperazine, that method includes reacting piperazine with 2-chloropyrimidine to obtain 1-(2-pyrimidyl)piperazine, which is then reacted with 3-chlorobutyronitrile to obtain the desired compound.

However, such a method has a number of drawbacks. Namely, the yields are relatively poor, and the starting material, 2-chloropyrimidine, is relatively expensive. The known method, as described in the references noted above, for producing the Formula II compounds entails a considerable waste of the expensive 2-chloropyrimidine. Part of the reason for the waste is that in reacting piperazine with 2-chloropyrimidine to obtain 1-(2-pyrimidyl)piperazine, a very significant amount of by-product comprising 1,4-bis(2-pyrimidyl)piperazine also results and must be separated out, thus wasting large amounts of 2-chloropyrimidine.

Accordingly, a need exists for alternative syntheses of the Formula II compounds which are more economical than the syntheses described in the prior art. The present invention provides such an alternative.

It should be noted that we also have invented other alternative syntheses of Formula II compounds and have invented other novel compounds which are useful in these syntheses. These other inventions are described in our co-pending U.S. patent applications, Ser. No. 407,215, filed Aug. 11, 1982, entitled "Acid Salts of 1-(Cyanoalkyl)-4-guanylpiperazines and Methods for Their Preparation and Use" and Ser. No. 407,223, filed Aug. 11, 1982, entitled "2-Pyrimidyl Alkanesulfonates and Methods for Their Preparation and Use," the disclosures of which are hereby incorporated herein by reference.

SUMMARY OF THE INVENTION

The invention provides a new method, more cost-efficient than the prior art method, for preparing 1-(cyanoalkyl)-4-(2-pyrimidyl)piperazines. The new method includes new intermediate methods and compounds.

The new compounds of the invention are cyanoalkylpiperazines represented by the structural formula

Formula III wherein R represents an alkylene group having from 1 to 5 carbon atoms.

One of the new methods of the invention is a method for preparing a compound represented by Formula III. The method comprises reacting piperazine with a haloalkylnitrile represented by the structural formula

X—R—CN    Formula IV wherein X represents a halo group and R is as previously defined, in the presence of an acid acceptor, to form a Formula III cyanoalkylpiperazine.

Another of the new methods of the invention is a method for preparing 1-(cyanoalkyl)-4-(2-pyrimidyl)piperazines represented by Formula II, starting with the new compounds of Formula III. The method comprises reacting a cyanoalkylpiperazine of Formula III with a 2-halopyrimidine in the presence of an acid acceptor to form a 1-(cyanoalkyl)-4-(2-pyrimidyl)piperazine represented by the structural formula

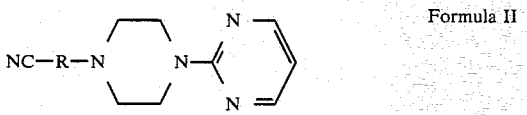

Formula II wherein R represents an alkylene group having from 1 to 5 carbon atoms.

A third method of the invention comprises a sequential combination of the two new methods described above. The method is one for preparing a 1-(cyanoalkyl)-4-(2-pyrimidyl)piperazine of Formula II, starting with piperazine. The method comprises reacting piperazine with a haloalkylnitrile of Formula IV in the presence of an acid acceptor to form a cyanoalkylpiperazine of Formula III and then reacting the cyanoalkylpiperazine with a 2-halopyrimidine in the presence of an acid acceptor to form the 1-(cyanoalkyl)-4-(2-pyrimidyl)piperazine.

DESCRIPTION OF PREFERRED EMBODIMENTS

The invention is described in detail below mainly in regard to specific preferred embodiments, wherein the alkylene group represented by R in Formulas II, III, and IV is a propylene group. Those are the specific embodiments that are involved in making use of the present invention in a reaction sequence to ultimately produce 8-[4-[4-(2-pyrimidyl)-1-piperazinyl]butyl]-8-azaspiro[4.5]decane-7,9-dione, a compound which also has been referred to in the prior art by the name buspirone and is known to be a particularly good tranquilizing and anti-emetic agent among those of Formula I. It is a particular purpose of the invention to provide means for more cost-efficient production of buspirone. However, unless otherwise stated below, it should be understood that any discussions of general or preferred reaction conditions, reagents, optional procedures, etc. are equally applicable to the remaining embodiments within the scope of the claimed invention, wherein the alkylene group represented by R is other than propylene.

Of the new compounds of the invention represented by Formula III, a particularly preferred embodiment is 1-(3-cyanopropyl)piperazine, because of its utility in preparing buspirone.

In accordance with a method of the invention, a Formula III compound is prepared by reacting piperazine with a Formula IV haloalkylnitrile in the presence of an acid acceptor under conditions sufficient to form the corresponding Formula III compound as the major product. Thus, in a particularly preferred embodiment 1-(3-cyanopropyl)piperazine, i.e.,

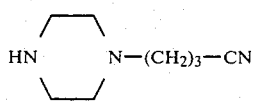

Formula V is prepared by reacting piperazine with a halobutyronitrile in the presence of an acid acceptor under conditions sufficient to form the Formula V compound as the major product. (In this regard, it should be noted that U.S. Pat. No. 3,196,155 briefly describes a method of reacting piperazine with 3-chlorobutyronitrile, but with reagents and conditions designed to give 1,4-bis(3-cyanopropyl)piperazine as the sole significant product).

Of the halobutyronitriles, chlorobutyronitrile and bromobutyronitrile are preferred reagents in the practice of the present method. They are readily available. The method can also be carried out with a reagent of mixed halobutyronitriles, and this is particularly preferred, because such mixtures are also readily available, operate adequately in this method, and are less expensive. For example, the method has been carried out successfully using a mixture of approximately 48–60 percent 3-chlorobutyronitrile, 35–41 percent 3-bromobutyronitrile, and the remainder glutaronitrile, by weight.

The method for producing 1-(3-cyanopropyl)piperazine is carried out in the presence of an acid acceptor to promote the condensation of piperazine with the halobutyronitrile. Excess piperazine can serve as the acid acceptor, but it is preferred to use one of the more common, less expensive bases, such as sodium carbonate, sodium bicarbonate, potassium carbonate, or potassium bicarbonate as the acid acceptor. In addition to being less expensive than using excess piperazine, use of such bases results in better yields of the Formula III compound. Sodium carbonate is a particularly preferred acid acceptor for this method.

The method for producing 1-(3-cyanopropyl)piperazine is most advantageously carried out in an organic solvent. A common organic solvent such as a lower (1–4 carbons) alkanol, acetone, or ethyl acetate is adequate. Acetone and ethyl acetate exhibit advantages during separation of products, and are, therefore, preferred solvents. Ethyl acetate is particularly preferred.

In carrying out the reaction, piperazine is preferably included in at least the stoichiometric amount for the 1 to 1 condensation. It is particularly preferred to include piperazine in excess of the stoichiometric amount (e.g., twice the stoichiometric amount) in order to promote better yields of 1-(3-cyanopropyl)piperazine by minimizing opportunities for creation of the di-substituted piperazine by-product, 1,4-bis(3cyanopropyl)piperazine. Yields of nearly 70% of the mono-cycanopropylpiperazine have been achieved by including piperazine in about twice the stoichiometric amount.

The condensation reaction of this method for producing 1-(3-cyanopropyl)piperazine is preferably carried out at reflux, and, since the reaction is exothermic, this is most easily accomplished by heating the piperazine and acid acceptor in solvent to reflux and then adding the halobutyronitrile as the final ingredient to the reaction mixture at a rate just sufficient to maintain reflux. It will then be necessary to heat the mixture, again, to maintain reflux until the reaction is complete. Upon completion of the condensation reaction, 1-(3-cyanopropyl)piperazine can be separated from other components of the final mix (e.g., from excess starting materials, such as piperazine and from by-products, such as 1,4-bis(3-cyanopropyl)piperazine), by distillation, preferably under reduced pressure.

In accordance with another method of the invention, a Formula III cyanoalkylpiperazine is reacted with a 2-halopyrimidine in the presence of an acid acceptor under conditions sufficient to form a 1-(cyanoalkyl)-4-(2-pyrimidyl)piperazine of Formula II. In a particularly preferred embodiment 1-(3-cyanopropyl)piperazine is reacted with a 2-halopyrimidine in the presence of an acid acceptor to form 1-(3-cyanopropyl)-4-(2-pyrimidyl)piperazine. This compound is particularly useful as a starting material for producing buspirone by the method described in the patents incorporated herein by reference above.

Of the 2-halopyrimidines, 2-chloropyrimidine is a preferred reagent for this method of producing Formula II compounds from Formula III compounds. Methods of preparing 2-chloropyrimidine are well known. For example, such a method is described in U.S. Pat. No. 4,256,888, which is hereby incorporated herein by reference.

The inventive method for producing Formula II compounds from Formula III compounds is carried out in the presence of an acid acceptor to promote condensation of the cyanoalkylpiperazine with the halopyrimidine. If the cyanoalkylpiperazine is included in excess, the excess amount can serve as the acid acceptor, but it is preferred instead to use one of the more common, less expensive bases, such as sodium carbonate, sodium bicarbonate, potassium carbonate, or potassium bicarbonate. Sodium carbonate is a particularly preferred acid acceptor for this method.

The method for producing Formula II compounds from Formula III compounds is most advantageously carried out in an organic solvent. A common organic solvent, such as acetone, ethyl acetate, or a lower alkanol having from 1 to 4 carbon atoms is adequate. Acetone and ethyl acetate are preferred solvents.

In carrying out the reaction the halopyrimidine, cyanoalkylpiperazine, and acid acceptor are brought together in the organic solvent, preferably in approximately the stoichiometric proportions for the reaction. The solution is heated at reflux. The resulting Formula II 1-(cyanoalkyl)-4-(2-pyrimidyl)piperazine can be separated out, e.g., by multiple extractions with cyclohexane, or by extraction with xylene and precipitation with heptane, or by distillation at reduced pressure.

In accordance with a third method of the invention, the two methods described above are carried out in sequence to produce a Formula II 1-(cyanoalkyl)-4-(2-pyrimidyl)piperazine by starting with piperazine. For example, in a particularly preferred embodiment of this method piperazine is reacted with a halobutyronitrile in the presence of an acid acceptor under conditions sufficient to form 1-(3-cyanopropyl)piperazine as the major product. This product is then reacted with a 2-halopyrimidine in the presence of an acid acceptor to form 1-(3-cyanopropyl)-4-(2-pyrimidyl)piperazine, which is a useful starting material for preparing the Formula I compound, buspirone, by the method described in the patents referenced herein under the Description Relative to the Prior Art.

All preferred conditions, reagents, etc. for the steps of the inventive method of producing Formula II compounds from piperazine are the same as those recited previously in the detailed description, hereinabove, of those steps as individual inventive methods.

The following Examples are presented to further illustrate some preferred embodiments of the invention.

EXAMPLE 1

Preparation of 1-(3-Cyanopropyl)piperazine from Piperazine

In a 5-liter 4-necked flask, equipped with an efficient stirrer, thermometer, condenser, and addition funnel, a slurry of 1292 g. (15.0 moles) piperazine and 930 g. (7.5 moles) sodium carbonate in 2.0 liters of ethyl acetate was stirred and heated to reflux (86° C.). The heat source was removed and from the funnel 975 g. (ca. 7.5 moles) of a mixture, comprising by weight about 60% 3-chlorobutyronitrile, about 35% 3-bromobutyronitrile, and the remainder glutaronitrile, was added at such a rate that a gentle reflux was maintained. Approximately one hour was required. Gas evolution ($CO_2$) was moderate during the addition but increased subsequently. The slurry was stirred and heated until the reaction was complete.

The reaction mixture was filtered, and the resulting solid cake was pressed down under a rubber dam. The solids were washed twice by slurrying in 1-liter portions of ethyl acetate. The combined filtrates were concentrated under vacuum to remove solvent and then the bulk of the excess piperazine. Finally the pot was heated to 150°–170° C. to distill the rest of the piperazine.

The product was subsequently distilled under high vacuum to give 1-(3-cyanopropyl)piperazine (melting point: 102.5°–103.5° C.), the structure of which was verified by IR, NMR, and TLC analytical techniques.

The total yield was 796 g. or 69.3% of the theoretical 1149 g. of 1-(3-cyanopropyl)piperazine.

The pot residue was found to comprise 1,4-bis(3-cyanopropyl)piperazine by-product.

EXAMPLE 2

Preparation of 1-(3-Cyanopropyl)-4-(2-pyrimidyl)piperazine from 1-(3-Cyanopropyl)piperazine A 500 mL, 3-neck flask equipped with thermometer, stirrer and condenser was charged with 150 mL of acetone, 75.2 g. (0.5 mole) of 1-(3-cyanopropyl)piperazine, 60 g. (0.525 mole) of 2-chloropyrimidine and 53 g. (0.48 mole) of sodium carbonate. The reaction mixture was heated at reflux until the reaction was complete. The resulting solids were removed by filtration and washed thoroughly with acetone. The filtrate and washes were combined and the solvent was removed under reduced pressure to give an orange solid. The solid was melted, 25 mL of water and 500 mL of cyclohexane were added, and the mixture was heated to reflux. The 3 phases were allowed to separate, and the top (cyclohexane) layer was decanted from the oil and water layers, evaporated under reduced pressure to about $\frac{2}{3}$ volume, seeded and cooled in an ice bath. The resulting solid was easily collected on a Buchner funnel and pressed thoroughly under a rubber dam until almost dry. The damp product was dried in an air oven to give 30.2 g. (26% yield) of 1-(3-cyanopropyl)-4-(2-pyrimidyl)piperazine as a first fraction.

Meanwhile the filtrate from the first fraction was combined with the oil and water phases. The mixture was heated to reflux and allowed to separate, and the cyclohexane solution was decanted as before. The solution was seeded and cooled in an ice bath. The product was collected and dried as previously to give 31.8 g. ($27\frac{1}{2}$% yield) of 1-(3-cyanopropyl)-4-(2-pyrimidyl)piperazine as a second fraction.

The filtrate from the second fraction was used in another extraction of the water and small residual oil phase to give 18.7 g. (16% yield) of 1-(3-cyanopropyl)-4-(2-pyrimidyl)piperazine as a third fraction. Analysis of the filtrate from the third fraction indicated that a fourth crop might have been possible, but this was not attempted.

The combined yield for all 3 fractions was 80.7 g. (70% yield) of 1-(3-cyanopropyl)-4-(2-pyrimidyl)piperazine, (melting point: 56°–58° C.), the structure of which was verified by NMR and TLC analytical techniques.

The invention has been described in detail with particular reference to certain preferred embodiments thereof, but it will be understood that variations and modifications can be effected within the spirit and scope of the invention.

What is claimed is:

1. A method for preparing a cyanoalkylpiperazine represented by the structural formula

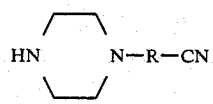

wherein R represents an alkylene group having from 1 to 5 carbon atoms, the method comprising reacting piperazine with a haloalkylnitrile represented by the structural formula

X—R—CN wherein X represents a halo group and R is as previously defined, in the presence of an acid acceptor, to form the cyanoalkylpiperazine.

2. The method of claim 1, wherein R represents a propylene group.

3. The method of claim 1, wherein X represents a chloro or bromo group.

4. The method of claim 1, wherein the acid acceptor comprises sodium carbonate.

5. The method of claim 1, wherein the method is carried out in an organic solvent.

6. The method of claim 5, wherein the organic solvent comprises acetone, ethyl acetate, or an alkanol having from 1 to 4 carbon atoms.

7. The method of claim 5, wherein the organic solvent comprises ethyl acetate.

8. A method for preparing a 1-(cyanoalkyl)-4-(2-pyrimidyl)piperazine represented by the structural formula

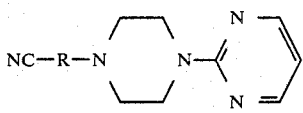

wherein R represents an alkylene group having from 1 to 5 carbon atoms, the method comprising reacting a cyanoalkylpiperazine represented by the structural formula

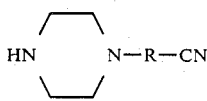

wherein R is as previously defined, with a 2-halopyrimidine in the presence of an acid acceptor to form the 1-(cyanoalkyl)-4-(2-pyrimidyl)piperazine.

9. The method of claim 8, wherein R represents a propylene group.

10. The method of claim 8, wherein the 2-halopyrimidine is 2-chloropyrimidine.

11. The method of claim 8, wherein the acid acceptor comprises sodium carbonate.

12. The method of claim 8, wherein the method is carried out in an organic solvent.

13. The method of claim 12, wherein the organic solvent comprises acetone, ethyl acetate, or an alkanol having from 1 to 4 carbon atoms.

14. The method of claim 12, wherein the organic solvent comprises acetone.

15. A method for preparing a 1(cyanoalkyl)-4-(2-pyrimidyl)piperazine represented by the structural formula

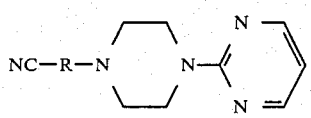

wherein R represents an alkylene group having from 1 to 5 carbon atoms, the method comprising the steps of:
(a) reacting piperazine with a haloalkylnitrile represented by the structural formula

X—R—CN wherein X represents a halo group and R is as previously defined, in the presence of an acid acceptor to form a cyanoalkylpiperazine represented by the structural formula

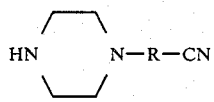

wherein R is as previously defined, and
(b) reacting the cyanoalkylpiperazine with a 2-halopyrimidine in the presence of an acid acceptor to form the 1-(cyanoalkyl)-4-(2-pyrimidyl)piperazine.

16. The method of claim 15, wherein R represents a propylene group.

17. The method of claim 15, wherein X represents a chloro or bromo group.

18. The method of claim 15, wherein the 2-halopyrimidine is 2-chloropyrimidine.

19. The method of claim 15, wherein at least one of steps (a) and (b) is carried out in the presence of an acid acceptor comprising sodium carbonate.

20. The method of claim 15, wherein at least one of steps (a) and (b) is carried out in an organic solvent.

21. The method of claim 20, wherein the organic solvent comprises acetone, ethyl acetate, or an alkanol having from 1 to 4 carbon atoms.

22. The method of claim 20, wherein the organic solvent comprises ethyl acetate or acetone.

* * * * *